(12) United States Patent
Teng et al.

(10) Patent No.: US 8,334,267 B2
(45) Date of Patent: Dec. 18, 2012

(54) MANGIFERIN CALCIUM SALTS, THE METHOD FOR ITS PREPARATION AND ITS USE

(75) Inventors: Houlei Teng, Haikou Hainan (CN); Wei Wu, Haikou Hainan (CN); Guang'ai Xu, Haikou Hainan (CN)

(73) Assignee: Hainan Deze Drug Research Co., Ltd., Haikou Hainan (CN)

( * ) Notice: Subject to any disclaimer, the term of this patent is extended or adjusted under 35 U.S.C. 154(b) by 337 days.

(21) Appl. No.: 12/744,263

(22) PCT Filed: May 23, 2008

(86) PCT No.: PCT/CN2008/001008
§ 371 (c)(1),
(2), (4) Date: May 21, 2010

(87) PCT Pub. No.: WO2009/065287
PCT Pub. Date: May 28, 2009

(65) Prior Publication Data
US 2010/0249046 A1    Sep. 30, 2010

(30) Foreign Application Priority Data

Nov. 22, 2007    (WO) ................. PCT/CN2007/071112

(51) Int. Cl.
*A01N 43/04*      (2006.01)
*A61K 31/70*      (2006.01)
*C07H 1/00*       (2006.01)
*C07H 15/04*      (2006.01)

(52) U.S. Cl. .......................... 514/23; 536/1.11; 536/120

(58) Field of Classification Search ................. 536/1.11, 536/120; 514/23
See application file for complete search history.

(56) References Cited

FOREIGN PATENT DOCUMENTS

| | | |
|---|---|---|
| CN | 1757648 A | 4/2006 |
| CN | 1919857 A | 2/2007 |
| CN | 101066275 A | 11/2007 |
| CN | 101108869 A | 1/2008 |

OTHER PUBLICATIONS

Miura et al., Phytomedicine, vol. 8(2) pp. 85-87, 2001.*
Miura et al., Biol. Pharm. Bull. 24(9), pp. 1091-1092, 2001.*
Liao Hongli et al., "Advanced research on the pharmacology of mangiferin", Tianjin Pharmacy, 2005, vol. 17, No. 2, pp. 50-52.

* cited by examiner

*Primary Examiner* — Traviss C McIntosh, III
(74) *Attorney, Agent, or Firm* — Birch, Stewart, Kolasch & Birch, LLP

(57) ABSTRACT

The present invention relates to novel mangiferin calcium and its preparation and use. The mangiferin calcium can lower plasma insulin, glucose, lipid, also can improve the solubility and oral bioavailability of mangiferin.

17 Claims, No Drawings

MANGIFERIN CALCIUM SALTS, THE METHOD FOR ITS PREPARATION AND ITS USE

FIELD OF THE INVENTION

The present invention relates to novel mangiferin calcium and their preparation methods and the use as the insulin sensitizer for diabetes and diabetic complication.

BACKGROUND OF THE INVENTION

Insulin resistance (IR) refers to a series of pathologic and clinical syndrome resulted from that the response of insulin target organs or tissues to the biological effects of insulin lowered or lost. Numerous studies show that insulin resistance exists in the whole process of type 2 diabetes, it is a marked characteristic of type 2 diabetes. The IR at the core, can lead to hyperglycemia, hypertension, microalbuminuria, inflammation, high fibrinolysis, dyslipidosis, endothelial dysfunction, and atherosclerosis and cardiovascular disease. Therefore, by increasing insulin action, improve insulin receptor sensitivity, research and development of insulin sensitizer in the treatment of diabetes and diabetic complication (Diabetic chronic complications refers to coronary heart disease, atherosclerosis, cerebrovascular disease and other diabetic macrovascular diseases, diabetic nephropathy, diabetic retinopathy and other diabetic microangiopathy, diabetic neuropathy, diabetic foot, diabetic maculopathy, diabetic cataract, diabetic glaucoma, refractive changes, iris and ciliary body diseases.) in recent years has become the hotspot.

At present, the most insulin sensitizers that are on the market are expensive or have some adverse reactions, caused poor compliance of patients. Therefore research and development of insulin sensitizers of low cost, high efficiency and low toxicity have important clinical significance and market value.

Mangiferin, a natural polyphenol is from *Anemarrhena asphodeloides* Bge. or the leaf of *Mangifera indical*, Anacardiaceae mango tree, the leaf, fruit or bark of *Mangifera persiciforma* C. Y Wu et T. L. Ming., gentian plants Northeast gentian, Swerita musstii Franch, or Pyrrosia clavata(Bak.) Ching. molecular weight:422, structural formula: $C_{19}H_{18}O_{11}$,

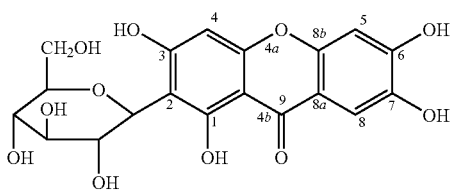

Mangiferin is a natural antioxidant. The pharmacological study shows Mangiferin has a variety of biological activity, such as anti-oxidation, anti-tumor, anti-bacterial, anti-viral, hypoglycemic, hypolipidemic, anti-inflammatory, choleretic, immunomodulation, etc. Mangiferin can lower the blood glucose and lipid levels of diabetic rats or mice by oral or intraperitoneal injection, its potential mechanism for hypoglycemic is by increasing insulin sensitivity [ Miura T, Ichiki H, Hashimoto I, et al. Antidiabetic activity of a xanthone compound, mangiferin. Phytomedicine, 2001, 8(2):85-87 ]. But mangiferin exists defects in solubility, the bioavailability and absorbability of the body.

SUMMARY OF THE INVENTION

In the course of present invention carrying out, we have obtained a series of salt compounds of mangiferin, which we have applied patent [ application No. CN200710129584.2; invention title: mangiferin salts and the method for preparation and their use ]. In that patent application we expatiated mangiferin salts can improve the solubility and oral bioavailability of mangiferin. As we research on pharmacology actives of increasing insulin sensitivity for these mangiferin salts, we found surprisingly that the mangiferin calcium not only improve the solubility and oral bioavailability of mangiferin, but also increase insulin sensitivity more strongly than mangiferin.

Technology Project:

In present invention, mangiferin calcium have the following characteristics:

① The chromatography characteristics of the mangiferin calcium is consistent with the standard mangiferin by HPLC.

② There is calcium ion in the structure of the mangiferin calcium.

In present invention, mangiferin calcium have the general formula (I):

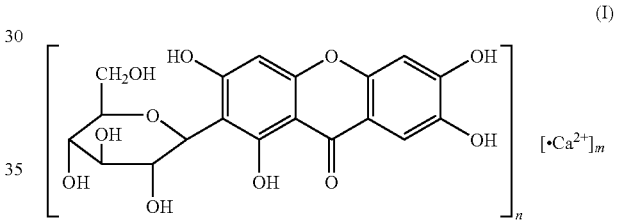

Wherein n is 1 or 2 and m is 1 or 2.

When n is 2 and m is 1, the mangiferin calcium has general formula (II):

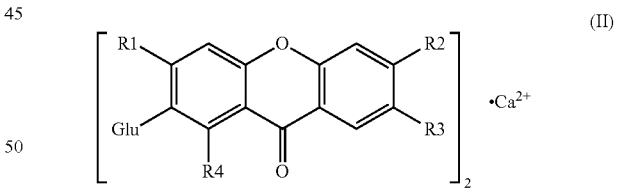

Where any radical of R1, R2, R3 and R4 is oxygen ion, the other radicals are hydroxyl. The priority elective compound has general formula:

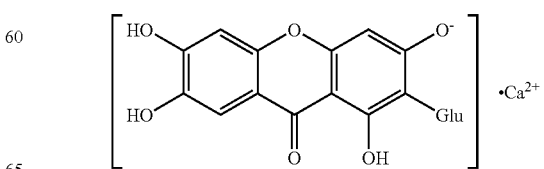

-continued

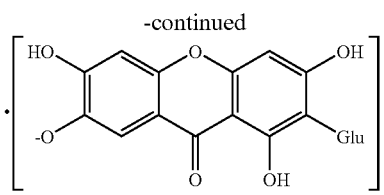

The present invention provides a method for preparation mangiferin calcium:

In present invention, mangiferin monosodium (or monopotassium) is obtained first, then mangiferin monosodium (or monopotassium) reacted with water-solubility calcium salt, and come into being mangiferin calcium. The method for preparation is as follows:

① mangiferin is suspended in menstruum, the solution of alkaline sodium (or potassium) is added slowly into the menstruum while mixing round until the solution is clear, then the reaction solution is filtrated, crystal menstruum is added into the reaction solution, mixing round adequately. A lot of deposition is come into being, the reaction solution is filtrated to get the deposition; the solid substance is heated up no excess 60° C. to dry. The yellow substance is mangiferin monosodium (or monopotassium).

② mangiferin monosodium (or monopotassium) is dissolved into water appropriated concentration, then water-solubility calcium salt solution of appropriated concentration is added slowly into it while mixing round. The reaction solution is mixed round to react completely. A lot of deposition is come into being in solution. The reaction solution is filtrated to get the deposition. This deposition is heated up no excess 60° C. to dry. The yellow solid substance is mangiferin calcium.

In the method of preparation as defined above, the mol ratio of mangiferin and alkaline sodium (or potassium) is 1:0.5-1.0.

In the method of preparation as defined above, the mol ratio of mangiferin monosodium (or monopotassium) and water-solubility calcium salt is 1:0.5.

In the method of preparation as defined above, the alkaline sodium (or potassium) is single salt or mixture which is for example sodium carbonate or sodium bicarbonate or potassium carbonate or potassium bicarbonate or sodium acetate or potassium acetate etc.

In the method of preparation as defined above, the water-solubility calcium salt is single salt or mixture which is for example calcium chloride, calcium gluconate, calcium lactate, calcium valerate, calcium glycerophosphate, iodized calcium, etc.

In the method of preparation as defined above, the menstruum is mixture, which water mixed with one or more than two kind of organic solvent for example ethanol or methanol or acetone which can dissolve water at discretion. The ratio of water is 10-90% (v/v).

In the method of preparation as defined above, the crystal menstruum is single organic solvent or mixture which is for example ethanol, acetone, ethyl acetate or chloroform, dichloromethane and the other.

In the invention mangiferin calcium maybe crystal water compounds, crystal water may be 0-9 mol.

The mangiferin calcium can be conducted through appropriate means of purification, such as filters, water rinse, and dry.

The mangiferin calcium in present invention can be obtained by the reaction of mangiferin with alkaline calcium compounds. The method for preparation is as follows:

Mangiferin is dissolved into appropriate solvent, and alkaline calcium compounds are dissolved into appropriate solvent, the alkaline solution is added into the mangiferin solution slowly while mixing round. Appropriate quantity solvent is added into reaction solution, a mass of yellow deposition appeared. The solution is filtrated to get deposition; the deposition is heated up no excess 60° C. to dry. The yellow green solid substance is calcium salt of mangiferin.

In the method for preparation as defined above, the mol ratio of mangiferin and alkaline calcium compounds is 1:0.5-2.

In the method for preparation as defined above, the alkaline calcium compound is single or mixture from which is inorganic calcium compounds or organic calcium compounds for example calcium hydroxide, calcium bicarbonate, calcium acetate, calcium propionate, etc. The priority elective compound is calcium hydroxide.

In the method for preparation as defined above, the solvents is single or mixture from which is the water solvent, dimethyl sulfoxide (DMSO), methanol, ethanol, acetone and other solvents.

In the process of research, we found phenomenon as follows:

1, The chromatography characteristics of the mangiferin calcium that was prepared by the above two methods is consistent with the standard mangiferin by HPLC.

2, There is calcium ion in the structure of mangiferin calcium that was prepared by the above two methods detected by titration.

3, The water solution of mangiferin calcium which mangiferin reacted with calcium hydroxide is unstable, it changes much in 2 hours. The reaction of mangiferin with other alkaline calcium like calcium bicarbonate or calcium acetate is difficult because they are alkalescent. The productivity is very low.

4, If mangiferin and calcium chloride are put together into water several ten days or heated up ten hours along, a little mangiferin calcium come into being in solution, which can be detected by HPLC, but the substance is too little to have industry value.

5, Mangiferin monosodium (or monopotassium) is come into being first; then mangiferin monosodium (or monopotassium) reacts with water-solubility calcium salt, and mangiferin calcium is come into being. The mangiferin calcium which is obtained by this method is stability, and the productivity is high.

According to the analysis and research above all, the method which mangiferin monosodium (or monopotassium) is come into being first, then mangiferin monosodium (or monopotassium) reacts with water-solubility calcium salt, and come into being mangiferin calcium is most excellent in the invention.

Identification of the Compound:

1, The compound identify of the mangiferin monosodium (or monopotassium):

① the NMR data of mangiferin:

The $^1$HNMR (DMSO-$d_6$) (δ ppm): The end proton of glucose signal is at 4.60 (1H, d, J=9.8 Hz), and it exist a beta-glycoside. Three phenyl proton signal is at 6.37 (1H, s), 6.86 (1H, s) and 7.39 (1H, s).

$^{13}$CNMR (DMSO-$d_6$) (δ ppm): 162.7 (C-1), 108.4 (C-2), 164.7 (C-3), 94.2 (C-4), 157.1 (C-4a), 102.2 (C-4b), 103.5 (C-5), 154.9 (C-6), 144.6 (C-7), 108.9 (C-8), 112.6 (C-8a), 151.7 (C-8b), 180.0 (C-9), 73.9 (C-1'), 71.5 (C-2'), 79.8 (C-3'), 71.1 (C-4'), 82.4 (C-5'), 62.4 (C-6').

② the NMR data of the mangiferin monosodium (or monopotassium):

The $^1$HNMR (DMSO-$d_6$) (δ ppm): The end proton of glucose signal is at 4.60 (1H, d, J=9.8 Hz), and it exist a beta-glycoside. Three phenyl proton signal is at 6.05 (1H, s), 6.19 (1H, s) and 6.95 (1H, s).

$^{13}$CNMR (DMSO-$d_6$) (δ ppm): 162.4 (C-1), 106.95 (C-2), 167.6 (C-3), 94.7 (C-4), 157.1 (C-4a), 101.7 (C-4b), 104.6 (C-5), 154.1 (C-6), 147.4 (C-7), 108.0 (C-8), 178.3 (C-9), 74.4 (C-1'), 71.0 (C-2'), 80.0 (C-3'), 71.0 (C-4'), 81.9 (C-5'), 61.8 (C-6').

Analysis the structural identification data of mangiferin monosodium (or monopotassium): The chemical shift of C-3 and C-7 displace to low-frequency magnetic field markedly in the $^{13}$CNMR data compared with mangiferin, The chemical shift of three phenyl proton displace to high-frequency magnetic field markedly in the $^1$HNMR data compared with mangiferin.

1-hydroxyl which conclude with 9-carbonyl in molecule can't react with alkalescent sodium (or potassium) because its acidity is weak. 3-hydroxyl and 7-hydroxyl can react with alkalescent sodium (or potassium) because its acidity is stronger. The acidity of 7-hydroxyl is slightly weaker than the acidity of 3-hydroxyl because 6,7-two hydroxyl conclude each other. When mangiferin react with sodium bicarbonate (potassium bicarbonate) (shortened form: bicarbonate route) by mol ratio of 1:1, the quantity of mangiferin-3-monosodium that the sodium is linked to the position C-3-hydroxy of mangiferin is more than the quantity of mangiferin-7-monosodium that the sodium is linked to the position C-7-hydroxy of mangiferin. When mangiferin react with sodium carbonate (potassium carbonate) (shortened form:carbonate route) by mol ratio of 1:0.5, the generation opportunities of mangiferin-3-monosodium and mangiferin-7-monosodium is equal because the alkalescence of sodium carbonate (potassium carbonate) is stronger than the alkalescence of sodium bicarbonate (potassium bicarbonate).

Therefore, we can prepare mangiferin monosodium by the reaction of mangiferin and sodium bicarbonate or sodium carbonate.

Based on the above analysis and data, we deduce the mangiferin monosodium is the mixture of mangiferin-3-monosodium and mangiferin-7-monosodium.

2, the compound identify of the mangiferin calcium:

the data of the mangiferin calcium:

ESI-MS m/z: 442 [M/2+H]$^+$, 423 [M$_{mgf}$+H]$^+$, we conjecture the molecular weight of the compound is 882; IR (KBr) cm$^-$: 3411, 3180 (shoulder, OH), 2926, 2900, 1650, 1620 (conjugate carbonyl), 1474 (phenyl).

The $^1$HNMR (DMSO-$d_6$) (δ ppm): The end proton of glucose signal is at 4.60 (1H, d, J=9.8 Hz), and it exist a beta-glycoside. Three phenyl proton signal is at 6.18 (1H, s), 6.25 (1H, s) and 7.05 (1H, s).

$^{13}$CNMR (DMSO-$d_6$)(δ ppm): 162.5 (C-1), 106.5 (C-2), 166.7 (C-3), 94.9 (C-4), 157.1 (C-4a), 102.2 (C-4b), 104.2 (C-5), 154.3 (C-6), 148.75 (C-7), 107.99 (C-8), 178.3 (C-9), 74.7 (C-1'), 71.1 (C-2'), 80.2 (C-3'), 71.1 (C-4'), 82.1 (C-5'), 61.8 (C-6').

Analysis the structural identification data of mangiferin calcium: The chemical shift of C-3 and C-7 displace to low-frequency magnetic field markedly in the $^{13}$CNMR data compared with mangiferin. The chemical shift of three phenyl proton displace to high-frequency magnetic field markedly in the $^1$HNMR data compared with mangiferin.

Our research shows that the productivity of mangiferin calcium that was prepared by bicarbonate route significantly is lower than that by carbonate route. The quantity of mangiferin-3-monosodium is more than the quantity of mangiferin-7-monosodium by bicarbonate route. In the process of reaction from mangiferin monosodium (monopotassium) to mangiferin calcium, because of molecule resistance of space, it is difficult to be obtained that the mangiferin calcium has the following formula:

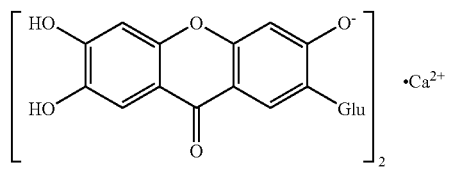

It is easy to be obtained that the mangiferin calcium has the following formula:

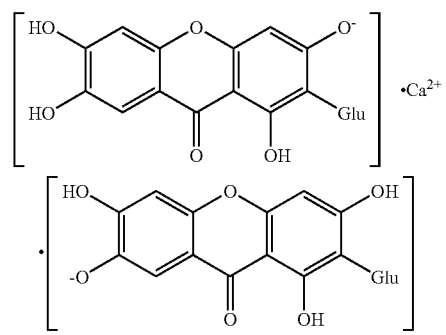

The generation opportunity of mangiferin-3-monosodium and mangiferin-7-monosodium is equal by carbonate route. The productivity of mangiferin calcium that was prepared by carbonate route is significantly higher than the productivity of mangiferin calcium that was prepared by bicarbonate route.

Based on above analysis and data, we deduce the structure of mangiferin calcium that is prepared through mangiferin monosodium (monopotassium) is as follows:

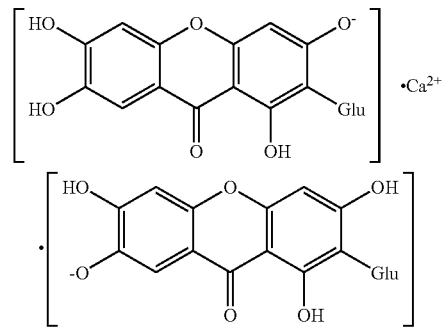

Mangiferin calcium may be prepared to clinic acceptable formulations with pharmaceutical acceptable auxiliary material. The formulations may be oral formulations or external formulations and injection formulations etc., for example tablets, capsules, gentle capsules, granules, pills, oral solution, oral suspension, gels and powder for injection etc.

The present invention also provides that mangiferin calciums are used as insulin sensitizers. These insulin sensitizers can also be used as hypoglycemic drugs, hypolipidemic drugs. As insulin sensitizers can be used for prevention and treatment of type 2 diabetes and diabetic chronic complications. Diabetic chronic complications refers to coronary heart disease, atherosclerosis, cerebrovascular disease and other diabetic macrovascular diseases; diabetic nephropathy, diabetic retinopathy and other diabetic microangiopathy; diabetic neuropathy, diabetic foot, diabetic maculopathy, diabetic cataract, diabetic glaucoma, refractive changes, iris and ciliary body diseases. As hypolipidemic drugs can be used for prevention and treatment hyperlipidemia.

The present invention provides that the effective dose range of mangiferin calcium is 10-80 mg/kg/day for the rats when mangiferin calcium is used as insulin sensitizers, In accordance with the different types of animal dose conversion formula discount to the human body for 100-800 mg/day/ person by oral administration, three times per day. Because of the difference between animals and the human body, so the adjustments of the actual clinical application dose and times can be allowed.

The invention is explained in detail in the examples given below which are provided by way of illustration only and therefore should not be construed to limit the scope of the invention.

EXAMPLES

The mangiferin in the invention can buy from market (the factory which have the correspond equipment can produce, for example Guangxi changzhou natural product Ltd.), mangiferin can separate from *Rhizoma Anemarrhenae* or leaves of *Mangifera indica* L. and other plants which have mangiferin. The reagent in present invention like sodium carbonate, sodium bicarbonate, potassium carbonate, potassium bicarbonate, sodium acetate, potassium acetate, calcium bicarbonate, calcium gluconate, ethanol, acetone, ethyl acetate, chloroform, dichloromethane etc. can buy from market. The standard mangiferin buy from China national institute for the control of pharmaceutical and biological products.

Example 1

Preparation of Mangiferin 100 kg *Rhizoma Anemarrhenae* are extracted by means of aqueous 80% ethanol two times at the temperature of 80° C. The combined extracts are evaporated. After the filtration the evaporated extract is placed into macfofeticulaf resin column to adsorb, the macrofeticulaf resin column is washed with water adequately. Mangiferin is unfixed by aqueous 40% ethanol, the solution is concentrated to obtained the crude mangiferin. The crude mangiferin is recrystallized from a mixture of solvents—dioxane-water to get pure mangiferin. The mangiferin samples are distinguished with mangiferin control, we acknowledged the samples are mangiferin. The purity of mangiferin is 98.5% detected by HPLC.

Identification of the Compound:

The $^1$HNMR (DMSO-$d_6$) ($\delta$ ppm): The end proton of glucose signal is at 4.60 (1H, d, J=9.8 Hz), and it exist a beta-glycoside. Three phenyl proton signal is at 6.37 (1H, s), 6.86 (1H, s) and 7.39 (1H, s).

$^{13}$CNMR (DMSO-$d_6$) ($\delta$ ppm): 162.7 (C-1), 108.4 (C-2), 164.7 (C-3), 94.2 (C-4), 157.1 (C-4a), 102.2 (C-4b), 103.5 (C-5), 154.9 (C-6), 144.6 (C-7), 108.9 (C-8), 112.6 (C-8a), 151.7 (C-8b), 180.0 (C-9), 73.9 (C-1'), 71.5 (C-2'), 79.8 (C-3'), 71.1 (C-4'), 82.4 (C-5'), 62.4 (C-6').

$^{13}$CNMR data of mangiferin in reference document【Y F Hong, G Y Han. ISOLATION AND STRUCTURE DETERMINATION OF XANTHONE GLYCOSIDES OF ANEMARRHENA ASPHODELOIDES.ACTA PHARMACEUTICA SINICA, 1997; 32 (6): 473-475】:

The $^1$HNMR (DMSO-$d_6$) ($\delta$ ppm): The end proton of glucose signal is at 4.60 (1H, d, J=9.8 Hz), and it exist a beta-glycoside. Three phenyl proton signal is at 6.46 (1H, s), 6.95 (1H, s) and 7.50 (1H, s).

$^{13}$CNMR (DMSO-$d_6$) ($\delta$ ppm): 161.6 (C-1), 107.3 (C-2), 163.6 (C-3), 93.9 (C-4), 156.1 (C-4a), 101.2 (C-4b), 102.5 (C-5), 153.6 (C-6), 143.7 (C-7), 108.1 (C-8), 118.7 (C-8a), 150.7 (C-8b), 179.0 (C-9), 73.0 (C-1'), 70.5 (C-2'), 78.8 (C-3'), 70.3 (C-4'), 81.3 (C-5'), 61.4 (C-6').

The compound that we prepared is consistent with the compound that is reported in the reference document, it is mangiferin.

Example 2

Preparation of Mangiferin Monosodium

Mangiferin 42.2 (0.1 mol) is suspended in the mixture of water 1800 ml and ethanol 600 ml in reactor, mixing round adequately. Sodium bicarbonate 8.4 g (0.1 mol) is dissolved in water, the concentration is 0.5% (w/v). The solution of sodium bicarbonate is added slowly into the mangiferin suspended solution while mixing round until the solution is clear, then the reaction solution is filtrated, appropriate quantity ethanol-ethyl acetate (1:1.5 v/v) is added into the reaction solution, mixing round adequately. A lot of deposition is come into being, the reaction solution is filtrated to get the deposition, the solid substance is heated up no excess 60° C. to dry. The yellow substance is mangiferin monosodium. Its weight is 31.2 g, the productivity is 74%. The purity of mangiferin monosodium is 98.6% detected by HPLC.

Example 3

Preparation of Mangiferin Monosodium

Mangiferin 42.2 (0.1 mol) is suspended in the mixture of water 1800 ml and ethanol 900 ml in reactor, mixing round adequately. Sodium carbonate 5.30 g (0.05 mol) is dissolved in water, the concentration is 0.5% (w/v). The solution of sodium carbonate is added slowly into the mangiferin suspended solution while mixing round until the solution is clear, then the reaction solution is filtrated, appropriate quantity acetone is added into the reaction solution, mixing round adequately. A lot of deposition is come into being, the reaction solution is filtrated to get the deposition; the solid substance is heated up not excess 60° C. to dry. The yellow substance is mangiferin monosodium. Its weight is 31.4 g, the productivity is 74.5%. The purity of mangiferin monosodium is 98.5% detected by HPLC.

Example 4

Preparation of Mangiferin Monopotassium

Mangiferin 42.2 (0.1 mol) is suspended in the mixture of water 200 ml and methanol 1800 ml in reactor, mixing round adequately. Potassium carbonate 6.9 g (0.05 mol) is dissolved in water, the concentration is 0.2% (w/v). The solution of potassium carbonate is added slowly into the suspended mangiferin solution while mixing round until the solution is clear, then the reaction solution is filtrated, appropriate quantity ethanol-chloroform (4:1 v/v) is added into the reaction solution, mixing round adequately. A lot of deposition is come into being, the reaction solution is filtrated to get the deposition; the solid substance is heated up no excess 60° C. to dry. The yellow substance is mangiferin monopotassium. Its weight is 31 g, the productivity is 73.4%. The purity of mangiferin monopotassium is 98.6% detected by HPLC.

Example 5

Preparation of Mangiferin Monopotassium

Mangiferin 42.2 (0.1 mol) is suspended in the mixture of water 1000 ml and methanol 1000 ml in reactor, mixing round adequately. Potassium bicarbonate 10.0 g (0.1 mol) is dissolved in water, the concentration is 0.1% (w/v). The solution of potassium bicarbonate is added slowly into the mangiferin suspended solution while mixing round until the solution is clear, then the reaction solution is filtrated, appropriate quantity ethanol-dichloroform (7:1 v/v) is added into the reaction solution, mixing round adequately. A lot of deposition is come into being, the reaction solution is filtrated to get the deposition; the solid substance is heated up no excess 60° C. to dry. The yellow substance is mangiferin monopotassium. Its weight is 31.7 g, the productivity is 75%. The purity of mangiferin monopotassium is 98.7% detected by HPLC.

Example 6

Preparation of Mangiferin Monosodium

Mangiferin 42.2 (0.1 mol) is suspended in the mixture of water 1800 ml and methanol 900 ml in reactor, mixing round adequately. Sodium carbonate 5.30 g (0.05 mol) is dissolved in water, the concentration is 5% (w/v). The solution of sodium carbonate is added slowly into the mangiferin suspended solution while mixing round until the solution is clear, then the reaction solution is filtrated, appropriate quantity ethyl acetate is added into the reaction solution, mixing round adequately. A lot of deposition is come into being, the reaction solution is filtrated to get the deposition, the solid substance is heated up no excess 60° C. to dry. The yellow substance is mangiferin monopotassium. Its weight is 32.3 g, the productivity is 76.5%. The purity of mangiferin monopotassium is 98.5% detected by HPLC.

Example 7

Preparation of Mangiferin Calcium

Mangiferin monosodium 4.44 g (0.01 mol) that is prepared by the method of example 2 is dissolved into 500 ml water, calcium chloride 0.55 g (0.005 mol) is dissolved in 150 ml water, calcium chloride solution is added slowly into mangiferin monosodium solution while mixing round, mixing round until it react completely. A lot of deposition is come into being in solution. The reaction solution is chilled in 4° C. more than 3 hours, then filtrated to get the deposition. The deposition is heated up no excess 60° C. to dry. The yellow solid substance is mangiferin calcium. Its weight is 2.7 g, the productivity is 61.4%. The purity of mangiferin calcium is 98.8% detected by HPLC.

Example 8

Preparation of Mangiferin Calcium

Mangiferin monosodium 4.44 g (0.01 mol) that is prepared by the method of example 3 is dissolved into 500 ml water, calcium chloride 0.55 g (0.005 mol) is dissolved in 150 ml water, calcium chloride solution is added slowly into mangiferin monosodium solution while mixing round, mixing round until it react completely. A lot of deposition is come into being in solution. The reaction solution is chilled in 4° C. more than 3 hours, then filtrated to get the deposition. This deposition is heated up no excess 60° C. to dry. The yellow solid substance is mangiferin calcium. Its weight is 3.4 g, the productivity is 77.2%. The pure of mangiferin calcium is 98.3% detected by HPLC.

Example 9

Preparation of Mangiferin Calcium mangiferin potassium 4.6 g (0.01 mol) that is prepared by the method of example 4 is dissolved into 300 ml water, calcium chloride 0.55 g (0.005 mol) is dissolved in 300 ml water, calcium chloride solution is added slowly into mangiferin potassium solution while mixing round, mixing round until it react completely. A lot of deposition is come into being in solution. The reaction solution is chilled in 4° C. more than 3 hours, then filtrated to get the deposition. This deposition is heated up no excess 60° C. to dry. The yellow solid substance is mangiferin calcium. Its weight is 3.5 g, the productivity is 76.3%. The pure of mangiferin calcium is 98.6% detected by HPLC.

Example 10

Preparation of Mangiferin Calcium mangiferin potassium 4.6 g (0.01 mol) that is prepared by the method of example 5 is dissolved into 300 ml water, calcium chloride 0.55 g (0.005 mol) is dissolved in 300 ml water, calcium chloride solution is added slowly into mangiferin potassium solution while mixing round, mixing round until it react completely. A lot of deposition is come into being in solution. The reaction solution is chilled in 4° C. more than 3 hours, then filtrated to get the deposition. This deposition is heated up no excess 60° C. to dry. The yellow solid substance is mangiferin calcium. Its weight is 2.9 g, the productivity is 63%. The pure of mangiferin calcium is 98.4% detected by HPLC.

Example 11

Preparation of Mangiferin Calcium

Mangiferin monosodium 4.44 g (0.01 mol) that is prepared by the method of example 3 is dissolved into 1000 ml water, calcium gluconate 2.15 g (0.005 mol) is dissolved in 150 ml water, calcium gluconate solution is added slowly into mangiferin monosodium solution while mixing round, mixing round until it react completely. A lot of deposition is come into being in solution. The reaction solution is chilled in 4° C. more than 3 hours, then filtrated to get the deposition. The deposition is heated up no excess 60° C. to dry. The yellow solid substance is mangiferin calcium. Its weight is 3.18 g, the productivity is 71.7%. The purity of mangiferin calcium is 98% detected by HPLC.

Example 12

Preparation of Mangiferin Calcium mangiferin 4.2 g (0.01 mol) is dissolved into 50 ml DMSO, calcium hydroxide 0.37 g (0.005 mol) is dissolved in 80 g glycerol, calcium hydroxide solution is added slowly into mangiferin solution while mixing round, mixing round until it react completely. Appropriate quantity ethanol is added into the reaction solution, mixing round adequately. A lot of deposition is come into being in solution. The reaction solution is filtrated to get the deposition. This deposition is heated up no excess 60° C. to dry. The yellow green solid substance is mangiferin calcium. Its weight is 3.8 g, the productivity is 90.4%. The purity of mangiferin monopotassium is 71.2% detected by HPLC.

Example 13

Preparation of Mangiferin Calcium mangiferin 4.2 g (0.01 mol) is dissolved into 80 ml DMSO, calcium hydroxide 1.48 g (0.02 mol) is dissolved in 200 g glycerol, calcium hydroxide solution is added slowly into mangiferin solution while mixing round, mixing round until it react completely. Appropriate quantity ethanol is added into the reaction solution, mixing round adequately. A lot of deposition is come into being in solution. The reaction solution is filtrated to get the deposition. This deposition is heated up no excess 60° C. to dry. The yellow green solid substance is mangiferin calcium. Its weight is 3.83 g, the productivity is 91.2%. The purity of mangiferin monopotassium is 63.8% detected by HPLC.

Example 14

Preparation of Mangiferin Calcium Capsules

The formulation is as follows:
mangiferine calcium 400 g carboxymethyl cellulose 300 g pregelatinized starch 300 g
the total is 10000 capsules.
Mangiferine calcium is obtained by the method of example 8 which is shattered into exiguous powder, mangiferine calcium and pregelatinized starch and carboxymethyl cellulose are put into together mixing round uniformity. Appropriate bond is spray in the powder to make soft material, which is cranked out granule. The granule is dried and then is put into capsules, 10000 capsules are prepared. There is 40 mg mangiferin calcium in every capsule.

Example 15

Preparation of Mangiferin Calcium Tablets

The formulation is as follows:
mangiferine calcium 500 g microcrystalline cellulose 200 g starch 300 g
The total is 10000 tablets.
mangiferine calcium is obtained by the method of example 8 which is shattered into exiguous powder, mangiferine calcium and starch and microcrystalline cellulose are put into together mixing round uniformity. Appropriate bond is spray in the powder to make soft material, which is cranked out granule. The granule is dried and then tablets are pressed by tablet pressed machine. 10000 tablets are prepared. There is 50 mg mangiferin calcium in every tablet.

Example 16

Preparation of Mangiferin Calcium Granule

The formulation is as follows:
mangiferin calcium 100 g carboxymethyl cellulose 300 g pregelatinized starch 300 g xylose 500 g
The total is 1000 g.
Mangiferin calcium is prepared by the method of example 8 which is shattered into exiguous powder, mangiferin calcium and pregelatinized starch and carboxymethyl cellulose and xylose are put into together mixing round uniformity. Appropriate bond is spray in the powder to make soft material, which is cranked out granule. The granule is dried. 1000 g granule is prepared. There is 100 mg mangiferin calcium in every gram.

Example 17

Preparation of Mangiferin Calcium Gel

The formulation is as follows:
mangiferine calcium 10 g tween80 2 g carbomer940 10 g sodium hydroxide 4 g ethanol 80 g
The surplus is distilled water
The total is 1000 g.
Mangiferin calcium is prepared by the method of example 8. Carbomer940 and Tween80 are mixed into water (solution 1), sodium hydroxide is dissolved in 100 ml water and added into solution 1, Gel matrix is obtained. Mangiferine calcium exiguous powder is dissolved in mixture of water and ethanol (solution 2). Solution 2 is added into gel matrix and mixed uniformity. The gel is Plus distilled water to 1000 g, mixing uniformity. That is mangiferin calcium gel.

Example 18

Preparation of Mangiferin Calcium Powder for Injection

The formulation is as follows:
mangiferine calcium 10 g mannitol 40 g
the surplus is distilled water
The total is 2000 ml.
Mangiferin calcium is prepared by the method of example 8. Mannitol is added into 1500 ml water for injection in appropriate containers, Activated carbon for injection is added into the solution and heated up to 80° C. while mixing round 30 min, then the solution is filtrated by microporous membrane of 0.22 nm (solution 1). Mangiferine calcium exiguous powder is dissolved in solution 1, Plus water for injection to 2000 ml, then the solution is filtrated by Microporous Membrane of 0.22 nm, the solution is separated into bottles, every bottle have 10 mg mangiferin calcium, all samples are freezed-drying. Stopers are pushed down after Freeze-drying, the bottles are airproof by covers; then stickers are pasted and packed up. That is mangiferin calcium powder for injection.

Mangiferin Calcium Detected by HPLC:
Apparatus: Angilent 1100 HPLC (American Agilent Co.), including G1312A dual pump G1313A Auto-Sampler.
Chromatographic Conditions:
Chromatographic column: discover ODS column (250 mm×6 mm, 5 μm);
The mobile phase: Acetonitrile—0.1% $H_3PO_4$ water (13:87 v/v)
Velocity of flow: 1.0 ml/min Detection Wavelength: 254 nm.

Column temperature: 30° C.

mangiferin calcium powder weighed up accurately is put into distilled water and dissolved, then the solution is determined in proper capacity. The tested samples solution is obtained.

Standard mangiferin powder weighed up accurately is put into methanol and dissolved, and then the solution is determined in proper capacity. The standard samples solution is obtained.

The tested samples solution and the standard samples solution are detected by HPLC separately. The data are recorded and calculated.

The chromatography characteristic of the mangiferin calcium that was prepared by the method of example 8 is consistent with that of the standard mangiferin by HPLC. The purity of mangiferin calcium is 98.3%.

The chromatography characteristic of the mangiferin calcium that was prepared by the method of example 12 is consistent with that of the standard mangiferin by HPLC. The purity of mangiferin calcium is 71.2%.

The Content of Calcium Ion in Mangiferin Calcium is Determined by Titration:

25 mg mangiferin calcium powder weighed up accurately is put into 20 ml distilled water and dissolved in taper glass bottle, and then 3 ml Buffer solution of $NH_3$-$NH_4Cl$ (pH=10) is added into the solution, a few eriochrome black T is added into the solution. Standard EDTA solution (0.0297 mol/L) is added into the solution until the solution color changed from wine red to yellow green. The content of calcium ion is calculated according to the volume of standard EDTA solution that is consumed by the sample. The results of four times experiments as follows:

| No. | Mangiferin calcium (by the method for preparation of example 8) | | Mangiferin calcium (by the method for preparation of example 12) | |
|---|---|---|---|---|
| | Mangiferin calcium (mg) | Calcium ion (mg) | Mangiferin calcium (mg) | Calcium ion (mg) |
| 1 | 23.2 | 0.95 | 22.7 | 1.07 |
| 2 | 28.2 | 1.31 | 27.5 | 1.31 |
| 3 | 25.5 | 1.18 | 26.5 | 1.25 |
| 4 | 27.5 | 1.28 | 29.5 | 1.37 |

The mol ratio of mangiferin ion and calcium ion is 2:1 according to the above calculation.

The Solubility of Calcium:

5 mg mangiferin powder which is weighed up accurately is put into 50 ml distilled water, the solution is shaked acutely 30 second every 5 minutes. The mangiferin can't be dissolved in 30 minutes. The water solubility of mangiferin is less than 0.1 mg/ml. Mangiferin is hardly solubility substance in water.

50 mg mangiferin calcium powder which is obtained by the method for preparation of example 8 and weighed up accurately is put into 50 ml distilled water, the solution is shaked acutely 30 second every 5 minutes, The mangiferin calcium can dissolve in 30 minutes.

100 mg mangiferin calcium powder which is obtained by the method for preparation of example 8 and weighed up accurately is put into 50 ml distilled water, the solution is shaked acutely 30 second every 5 minutes. The mangiferin calcium can not dissolve completely in 30 minutes.

The water solubility of mangiferin calcium is more than 1 mg/ml. Mangiferin is tiny solubility substance in water.

The Pharmacokinetics of Mangiferin and Mangiferin Calcium after Oral Administration 1, The Confect of Drug Solution Mangiferin is suspended in Carboxymethyl cellulose sodium solution which concentration is one percent; the mangiferin concentration is 10 mg/mL, which is sample A.

Mangiferin calcium is suspended in Carboxymethyl cellulose sodium solution which concentration is one percent; the mangiferin concentration is 10 mg/mL, which is sample B. The mangiferin calcium is obtained by the method for preparation of example 8.

2, Oral Administrated Project

All rats were fasted for 16 hours, free drinking water. The rats are oral administrated separately sample A and sample B, which dose is 100 mg/kg. The rats were taken whole blood in 5 minutes before oral administrated and 15 min, 30 min, 45 min, 60 min, 90 min, 120 min, 180 min, 240 min, 300 min, 360 min, 480 min after oral administrated. Serum is separated from these blood samples.

3, Serum Sample Treatment

Serum Samples are extracted accurately 0.2 ml into centrifuge tubes separately; then 40 µL cold trichloroacetic acid solution which concentration is ten percent is added into centrifuge tubes separately. The samples are whorled 3 minutes; then centrifuged 12000 r/min for 10 minutes, 120 µl the up layer solution are extracted from centrifuge tubes and put into sample bottles separately. All the samples are detected by HPLC.

Apparatus: Angilent 1100 HPLC (American Agilent Co.), include G1312A dual pump G1313A Auto-Sampler.

Chromatographic Conditions:

Chromatographic column: discover ODS column (250 mm×6 mm, 5 µm);

The mobile phase: Acetonitrile—0.1% $H_3PO_4$ water (13:87 v/v)

Velocity of flow: 1.0 ml/min

Detection Wavelength: 254 nm.

Column temperature: 30° C.

4, Results:

According to the data (Table 1), the pharmacokinetics data of oral administrated mangiferin calcium is better than oral administrated mangiferin. The bioavailability of mangiferin calcium is better than mangiferin.

TABLE 1

The Pharmacokinetics parameter of mangiferin calcium and mangiferin

| parameter | mangiferin | mangiferin calcium |
|---|---|---|
| Cmax/µg/ml | 14.8 ± 0.5 | 48.3 ± 0.6 |
| $T_{1/2}\beta$ (min) | 45.7 ± 8.3 | 61.4 ± 7.7 |
| $AUC_{0-\infty}$/µg · h/ml | 1864.1 ± 275.2 | 3469.2 ± 359.3 |

Efficacy in STZ Model

1, Materials

Mangiferin calcium is prepared in accordance with the method of preparation of example 12. Mangiferin are prepared in accordance with the method of preparation of example 1. Rosiglitazone Hydrochloride tablets were purchased from Zhejiang wanma pharmaceutical Co., Ltd. Mangiferin and mangiferin calcium salts were suspended with 3% sodium carboxymethyl cellulose.

Normal female wistar rats (SPF, 3 months age, 180-200 g) were purchased from Hainan provincial peoples hospital experimental Animal Center. The animals were kept in a room temperature (25~28° C.) with free access of food and water. A light-dark cycle (6 a.m and 6 p.m) was strictly enforced. High fat chow is composed of 55% basic chow, 2% protein, 16% fat, 27% white sugar.

2, Method

Model: After the rats were fasted for 12 hours, the rats are injected 30-35 mg/kg streptozotocin (STZ) solution once by tail vein. STZ solution is prepared to 2% concentration with 0.1 mmol/L, pH 4.4 citrate-sodium citrate buffer before use. The model rats were weighed, taked out tail vein blood, tested blood glucose when the Model is done after 14 days after fasting for 12 hours, then injected 20% glucose solution (2 mg/kg) by intraperitoneal, determined blood glucose in 0.5 h, 1 h, 2 h. The rats whose glucose tolerance is abnormal were brought into experiments. Normal wistar rats were fed normal chow, model rats were fed high fat chow.

Experimental group:normal wistar rats group (n=10); after Diabetes model is succeed, the rats were randomly divided into 7 groups: Diabetes model group (n=10); mangiferin groups (20, 40, 80 mg/kg, each 10 rats); mangiferin calcium groups (10, 20, 40 mg/kg, each 10 rats); Rosiglitazone Hydrochloride group [3 mg/kg, n=10]. Test samples or vehicle control was given orally for 8 weeks. Diabetes model group and normal group were given vehicle.

Measurements:

Determination of insulin sensitivity (Glucose infusion rate): Using glucose clamp technique, in accordance with Konglingdong'method 【KONG Ling-dong, ZHU Liang-zheng, SONG Ju-min, etc al. Intervention Effects of Tiaozhi Jiangtang Tablet on Insulin Resistance in Rats with Diabetes Mellitus Type 2. Chinese Journal of Integrated Traditional and Western Medicine, 2006, 26:76-79】 in the treatment of eight weeks.

Determination of plasma glucose and lipid: Rats were taken whole blood after killed, then serum was separated, determined plasma glucose (GLU), insulin (INS), triglycerides (TG) and free fatty acids (FFA).

GLU and TG levels were determined using GF-D800 semi-auto chemist which was purchased from Shandong Gaomi Caihong Analytical Instrument Co., Ltd. Free fatty acids were determined using copper colorimetric determination. The kits for Determination of free fatty acids were purchased from Nanjing Jiancheng Bioengineering Institute. Insulin: radio-immunoassay (RIA), γ counter counts. insulin RIA Kit was purchased from Shandong Weifang City three-dimensional (3V) Biological company.

Statistics: The results have been calculated as mean±SD ($\bar{x}$±SD) and compareisons of the data have been done by t-test.

3, Results 20 mg/kg mangiferin does not significantly improve GLU, TG, FFA, INS, Glucose infusion rate in diabetic rats. 10 mg/kg mangiferin calcium can significantly improves GLU, TG, FFA, INS, Glucose infusion rate in diabetic rats and has a significant dose-effect relationship (Table 2).

These results suggest that mangiferin calcium can improve the solubility, oral bioavailability and pharmacological activity of mangiferin because the effective doses of mangiferin calcium are greatly reduced than mangiferin.

Efficacy in GK Model

1, Materials

Mangiferin calcium is prepared in accordance with the method of preparation of example 8. Mangiferin are prepared in accordance with the method of preparation of example 1. Rosiglitazone Hydrochloride tablets were purchased from Zhejiang wanma pharmaceutical Co., Ltd. Mangiferin and mangiferin calcium were suspended with 3% sodium carboxymethyl cellulose before use.

Goto-Kakizaki rats (GK) (16 weeks age, ♀ ♂) were purchased from Shanghai SLAC laboratory animal Co., Ltd. The animals were kept in IVC cages with temperature (22° C.). There are two rats in each cage.

2, Method

Experimental group: GK rats group (n=10); mangiferin groups (20, 40, 80 mg/kg, each 10 rats); mangiferin calcium groups (10, 20, 40 mg/kg, each 10 rats); Rosiglitazone Hydrochloride group [3 mg/kg, n=10]. Test samples or vehicle control was given orally for 30 days. GK rats group were given vehicle.

Measurements:

The blood specimens were taken by abdominal aorta at the end of the test. Plasma glucose (GLU), insulin (INS), triglycerides (TG), total cholesterol (TC), high density lipoprotein (HDL), low density lipoprotein (LDL) were determined GLU, TC, TG, HDL and LDL levels were determined using GF-D800 semi-auto chemist which was purchased from Shandong Gaomi Caihong Analytical Instrument Co., Ltd. Insulin: radioimmunoassay (RIA), γ counter counts. insulin RIA Kit was purchased from Shandong Weifang City three-dimensional (3V) Biological company.

Statistics: The results have been calculated as mean±SD ($\bar{x}$±SD) and comparisons of the data have been done by t-test.

3, Results 20 mg/kg mangiferin does not significantly improve GLU, TC, TG, HDL and LDL and INS in diabetic GK rats. 40 mg/kg mangiferin improves TG, HDL and LDL in diabetic GK rats. 10 mg/kg mangiferin calcium can significantly improves TC, HDL and LDL in diabetic GK rats. 20 mg/kg mangiferin calcium can significantly improves GLU, TC, TG, HDL and LDL and INS in diabetic GK rats (Table 3).

These results suggest that mangiferin calcium can improve the solubility, oral bioavailability and pharmacological activity of mangiferin because the effective doses of mangiferin calcium are greatly reduced than mangiferin.

TABLE 2

Effect of the samples in STZ rats

| Groups | GLU (mmol/L) | INS (μ IU/ml) | TG (mmol/L) | FFA (μmol/L) | Glucose infusion rate (mg/kg · min) |
|---|---|---|---|---|---|
| Normal group | 6.37 ± 0.39** | 20.67 ± 4.39** | 1.38 ± 0.11** | 1.08 ± 0.12** | 26.25 ± 4.24** |
| Model group | 11.43 ± 0.42 | 37.39 ± 3.56 | 3.62 ± 0.37 | 1.88 ± 0.20** | 14.46 ± 3.87** |
| Mangiferin group (20 mg/kg) | 10.56 ± 0.38 | 33.42 ± 3.79 | 3.42 ± 0.41 | 1.79 ± 0.24 | 15.75 ± 3.69 |
| Mangiferin group (40 mg/kg) | 8.45 ± 0.23* | 28.13 ± 3.74* | 2.82 ± 0.22* | 1.56 ± 0.19* | 18.32 ± 3.89* |
| Mangiferin group (80 mg/kg) | 7.05 ± 0.44** | 24.35 ± 3.46** | 1.82 ± 0.32** | 1.29 ± 0.34** | 23.65 ± 3.67** |
| Mangiferin calcium group (10 mg/kg) | 8.01 ± 0.32* | 27.63 ± 3.46* | 2.49 ± 0.18* | 1.54 ± 0.23* | 17.56 ± 3.45* |
| Mangiferin calcium group (20 mg/kg) | 7.31 ± 0.22** | 23.57 ± 3.68** | 1.93 ± 0.36** | 1.28 ± 0.14** | 24.37 ± 3.75** |
| Mangiferin calcium group (40 mg/kg) | 6.91 ± 2.02** | 20.53 ± 4.42** | 1.49 ± 0.28** | 1.13 ± 0.18** | 26.36 ± 3.58** |
| Rosiglitazone group | 7.49 ± 2.18** | 19.87 ± 4.21** | 1.44 ± 0.16** | 1.25 ± 0.13** | 24.75 ± 3.69** |

Table 1: compared with model group: *p < 0.05, **p < 0.01.

TABLE 3

Effect of the samples in GK rats

| Groups | Weigh g | GLU mmol/L | TG mmol/L | TC mmol/L | LDL mmol/L | HDL mmol/L | INS μ IU/ml |
|---|---|---|---|---|---|---|---|
| GK group | 321.38 ± 16.07 | 23.66 ± 3.34 | 2.11 ± 0.57 | 2.66 ± 0.19 | 1.58 ± 0.19 | 0.67 ± 0.06 | 35.23 ± 14.25 |
| Rosiglitazone group | 323.10 ± 24.40 | 24.38 ± 2.26 | 1.48 ± 0.12** | 2.40 ± 0.17** | 1.37 ± 0.19** | 0.78 ± 0.07** | 17.58 ± 9.80* |
| Mangiferin calcium group (10 mg/kg) | 318.63 ± 16.94 | 24.06 ± 1.57 | 1.79 ± 0.22 | 2.43 ± 0.21* | 1.26 ± 0.18** | 0.81 ± 0.07*** | 27.48 ± 8.70 |
| Mangiferin calcium group (20 mg/kg) | 307.15 ± 13.67 | 23.34 ± 1.67 | 1.60 ± 0.41* | 2.47 ± 0.08* | 1.31 ± 0.10* | 0.80 ± 0.10** | 20.45 ± 6.36* |
| Mangiferin calcium group (40 mg/kg) | 307.61 ± 13.88 | 23.17 ± 1.58 | 1.57 ± 0.39* | 2.49 ± 0.07* | 1.37 ± 0.11* | 0.80 ± 0.09** | 16.79 ± 5.37* |
| Mangiferin group (20 mg/kg) | 319.56 ± 21.50 | 19.65 ± 5.07 | 1.69 ± 0.31 | 2.54 ± 0.28 | 1.56 ± 0.26 | 0.68 ± 0.12 | 26.94 ± 4.89 |
| Mangiferin group (40 mg/kg) | 311.85 ± 10.40 | 20.33 ± 4.09 | 1.61 ± 0.22* | 2.50 ± 0.45 | 1.33 ± 0.41* | 0.75 ± 0.13* | 24.44 ± 1.91 |
| Mangiferin group (80 mg/kg) | 312.67 ± 10.43 | 20.57 ± 4.13 | 1.59 ± 0.16* | 2.45 ± 0.31* | 1.30 ± 0.38* | 0.78 ± 0.11* | 16.68 ± 1.76* |

Table 2: compared with GK group: *$P < 0.05$; $P < 0.01$; *$P < 0.001$.

The invention claimed is:

1. A mangiferin calcium, wherein the mangiferin calcium has the formula (I):

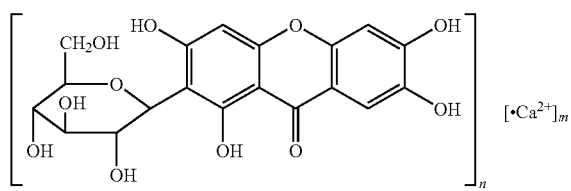

(I)

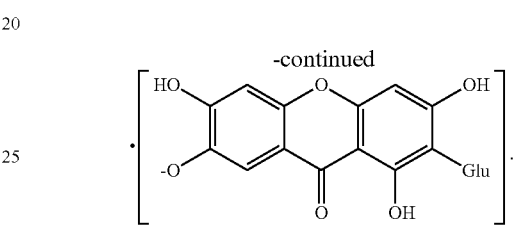

-continued wherein n is 1 or 2 and m is 1 or 2.

2. The mangiferin calcium according to claim 1, wherein when n is 2, m is 1, the mangiferin calcium have general formula (II):

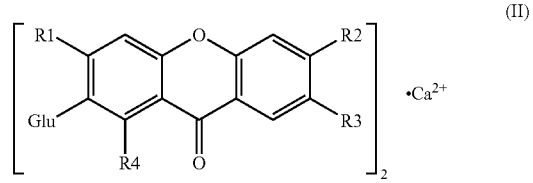

(II)

Where any radical of R1, R2, R3 and R4 is oxygen ion, the other radicals are hydroxyl.

3. The mangiferin calcium according to claim 2, wherein the mangiferin calcium have following formula:

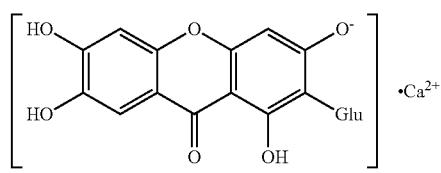

4. A method for the preparation of the mangiferin calcium according to claim 3, wherein:

① mangiferin react with alkaline sodium or alkaline potassium, and come into being mangiferin monosodium or mangiferin monopotassium;

② mangiferin monosodium or mangiferin monopotassium reacted with water-solubility calcium salt, and come into being mangiferin calcium.

5. The method according to claim 4, wherein the mol ratio of mangiferin and alkaline sodium or alkaline potassium is 1:0.5-1.0.

6. The method according to claim 4, wherein the mol ratio of mangiferin monosodium or mangiferin monopotassium and water-solubility calcium salt is 1:0.5.

7. The method according to claim 4, wherein the alkaline sodium or alkaline potassium is single salt or mixture which is sodium carbonate, sodium bicarbonate, potassium carbonate, potassium bicarbonate, sodium acetate and potassium acetate.

8. The method according to claim 4, wherein the water-solubility calcium salt is single salt or mixture which is calcium chloride, calcium gluconate, calcium lactate, calcium valerate, calcium glycerophosphate, iodized calcium.

9. A pharmaceutical composition, which comprises any effective amount of a mangiferin calcium as defined in claim 1, and a pharmaceutically acceptable auxiliary material.

10. A pharmaceutical composition, which comprises an effective amount of a mangiferin calcium as defined in claim 3, and a pharmaceutically acceptable auxiliary material.

11. A pharmaceutical composition according to claim 9, wherein the formulations can be tablets, capsules, gentle capsules, granules, pills, oral solution, oral suspension, gels and powder for injection.

12. An insulin sensitizer, comprising:
mangiferin calcium as defined in claim 1.

13. An insulin sensitizer, comprising:
mangiferin calcium as defined in claim 3.

14. A hypoglycemic drug, comprising:
the insulin sensitizer of claim 13.

15. A hypolipidemic drug, comprising:
the insulin sensitizer of claim 13.

16. A method for treating type 2 diabetes, comprising:
administering an effective amount of the insulin sensitizer of claim 13 to a patient in need thereof.

17. An insulin sensitizer, comprising:
the pharmaceutical composition as defined in claim 10.

\* \* \* \* \*